United States Patent [19]

Kouge

[11] Patent Number: 4,990,644

[45] Date of Patent: * Feb. 5, 1991

[54] SULFONIUM COMPOUND AND ACYLATING AGENT

[75] Inventor: Katsushige Kouge, Yamaguchi, Japan

[73] Assignee: Sanshin Kagaku Kogyo Co. Ltd., Yamaguchi, Japan

[*] Notice: The portion of the term of this patent subsequent to Aug. 15, 2006 has been disclaimed.

[21] Appl. No.: 320,656

[22] Filed: Mar. 8, 1989

[30] Foreign Application Priority Data

Mar. 8, 1988 [JP] Japan ................................ 63-55856

[51] Int. Cl.$^5$ ............................................ C07C 141/02
[52] U.S. Cl. ................................................... 558/20
[58] Field of Search ................................. 558/20, 271

[56] References Cited

U.S. PATENT DOCUMENTS 4,857,656 8/1989 Kouge ................................ 558/271

OTHER PUBLICATIONS

E. Fisher, Chem. Ber., 36, 2094-2106 (1903).
Th. Curtius, Chem. Ber., 35, 3226-3228 (1902).
H. G. Khorana, J. Chem. Soc., 1952, 2081-2088.
Th. Wieland et al., Justus Liebigs Annalen der Chemie, 569, 117-121 (1950).
M. Bodanszky et al., J. Amer. Chem. Soc., 81, 5688-5691 (1959).
J. Kovacs, M. Q. Ceprini, Chemistry & Industry, 1965, 2100.
G. W. Anderson et al., J. American Chem. Soc., 85, 3039 (1963).
Chem. Abstr., 103, 196393t.
Preliminary Lecture Draft—52nd Annual Meeting of the Japanese Chemical Association and Translation Thereof.
Katsushige Kouge et al., "Peptide Synthesis in Aqueous Solution. I. Application of p–Dialkyl–Sulfoniophenols as a Water–Soluble Coupling Reagent", Bull. Chem. Soc. Jpn. 60,2409–2418 (1987).

*Primary Examiner*—Nicky Chan
*Attorney, Agent, or Firm*—Sandler, Greenblum & Bernstein

[57] ABSTRACT

It has been found that the 9-fluorenylmethoxycarbonylating agent according to the present invention can contribute, for example, to the biochemical field as a useful long-chained acylating reagent as described in examples.

1 Claim, No Drawings

SULFONIUM COMPOUND AND ACYLATING AGENT

FIELD OF THE INVENTION

The invention relates to a novel sulfonium compound and an acylating agent enabling 9-fluorenylmethoxy carbonylating reagents to react with an amino or imino group using a novel 9-fluorenylmethoxy carbonyloxyphenyl dimethylsulfonium compound, and more particularly, 9-fluorenylmethoxy carbonylation in an aqueous solution.

DISCUSSION OF BACKGROUND AND MATERIAL INFORMATION

For the chemical synthesis of peptides, particularly, regarding the protection group for the amino group, 9-fluorenylmethoxy carbonyl group capable of disconnection under a weakly basic condition has attracted attention.

Heretofore, 9-fluorenylmethoxy carbonyl chloride has been known as a typical reaction reagent as the 9-fluorenylmethoxy carbonylation reagent. However, although this reagent is excellent in view of its reactivity, it has poor stability and requires use in excess amounts for the reaction to proceed, particularly, in an aqueous solution. In addition, it is stimulating and requires care upon handling. In order to overcome such problems, there have recently been developed active esters of 9-fluorenylmethoxy carbonylating reagents prepared by introducing an acyl amide portion to pentachlorophenol, p-nitrophenol, N-hydroxysuccinimide or active amide type acylating reagents represented by acyl imidazoles.

However, since these 9-fluorenylmethoxy carbonylating reagents have no water-solubility or hydrophilic property on the compound per se. Unfortunately, it is necessary to dissolve them in an organic solvent compatible with water, in the case of reaction in an aqueous solution, and then conduct the reaction with a substrate in the aqueous solution. Then, for recovering the reaction product, the organic solvent has to be distilled off from the reaction system.

Furthermore, since the removal of hydroxy compounds formed by the reaction is difficult, no satisfactory purity can be obtained, depending on the case, unless recrystallization or chromatographic purification is applied. Further, in the case of using those compounds instable in the organic solvent, for example, proteins or peptides as the substrate, the efficiency of the reaction is extremely reduced.

SUMMARY OF THE INVENTION

The present invention concerns a novel sulfonium compound represented by the following formula and the application use thereof:

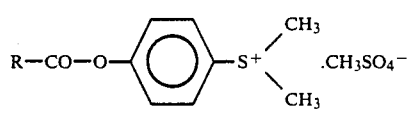

where R represents a 9-fluorenylmethoxy group.

DETAILED DESCRIPTION OF THE INVENTION

A preferred embodiment of the invention involves a sulfonium compound represented by the general formula:

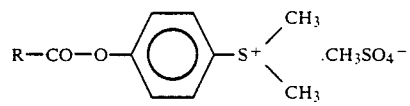

where R represents 9-fluorenylmethoxy group.

Another preferred embodiment involves a 9-fluorenylmethoxy carbonylating agent of a sulfonium compound represented by the following formula:

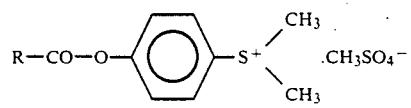

where R represents a 9-fluorenylmethoxy group.

Another embodiment involves use of an acylating agent comprising sulfonium compound represented by the general formula:

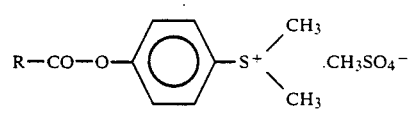

where R represents 9-fluorenylmethoxy group.

Another embodiment involves the chemical synthesis of peptides using a 9-fluorenylmethoxy carbonylating agent of a sulfonium compound represented by the following formula:

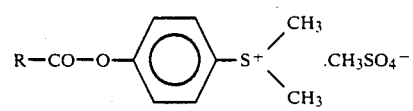

where R represents a 9-fluorenylmethoxy group, which is capable of disconnection under a weakly basic condition.

The present inventor has been able to overcome the foregoing drawbacks in the prior art covering 9-fluorenylmethoxy carbonylating reagents and has unexpectedly found a novel sulfonium compound represented by the general formula:

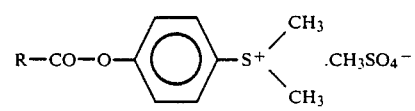

where R represents a 9-fluorenylmethoxy group, which has an excellent acylating function in an aqueous solution.

The present compound can be obtained through the reaction of 4-hydroxyphenyl dimethylsulfonium methylsulfate and a 9-fluorenylmethoxy carbonyl chloride. This reaction is more fully described in Applicants copending application, U.S. Ser. No. 023,251 which disclosure is incorporated herein by reference.

The unique feature of the compound according to the present invention as the 9-fluorenylmethoxy carbonylating reagent is that the compound itself is water-soluble and, accordingly, it has become possible to use the 9-fluorenylmethoxy-carbonylating reagent to react with those living body specimens such as amino acids, peptides, proteins, etc. The reaction is performed easily under moderate conditions in an aqueous solution which has been difficult so far. In addition, since the reaction is conducted in the aqueous solution, it is also possible to adjust the pH value in the aqueous solution to selectively acylate only the α-amino group or side chain amino group of amino acids or peptides.

The invention will be further appreciated by the following example which illustrates two embodiments of the instant invention. All percentages throughout the specification and claims are by weight of the total composition unless otherwise indicated.

EXAMPLE

Synthesis of 4-(9-fluorenylmethoxycarbonyloxy) phenyl dimethylsulfonium methylsulfate 13.3 g (0.05 mol) 4-hydroxyphenyldimethylsulfonium methylsulfate was dissolved into 200 ml of acetonitrile and, while stirring under ice cooling, 7 ml (0.05 mol) of triethylamine was added dropwise. After stirring for 20 minutes at that temperature, 15.5 g (0.06 mol) of 9-fluorenylmethoxycarbonyl chloride was gradually added and stirred for 3 hours.

The reaction solution was filtered, the filtrate was concentrated under a reduced pressure and the residue was recrystallized with addition of ethyl acetate. Results are as follows:

Yield: 20.7 g (85.0%)
Melting point: 76.0° -80.0° C.
IR: 1740 cm$^{-1}$, 1780 cm$^{-1}$ (C=0)
Elemental analysis:
Theoretical value $C_{24}H_{24}O_7S_2$.
C: 59.03%, H: 4.92%.
Measured value.
C: 59.25%, H: 4.90%.

REACTION EXAMPLE

Synthesis of N-9-fluorenylmethoxy carbonyl amino acid

Various amino acids in the amount of 0.01 mol were dissolved into 21 ml of an aqueous 10% sodium carbonate solution and, under stirring at room temperature (20° -24° C.), 4.88 g (0.01 mol) of 4-(9-fluorenylmethoxycarbonyloxy) phenyldimethylsulfonium methylsulfate was added and reacted under room temperature (20° -24° C.) for 12 hours. The reaction solution was rendered acidic with addition of 6N-HCl and extracted with ethyl acetate. The ethyl acetate layer was dried with anhydrous sodium sulfate and the residue obtained by distillation under a reduced pressure was crystallized with addition of petroleum ether. The results are shown in the following table.

TABLE

Synthesis of 9-fluorenylmethoxy carbonyl amino acids using 9-fluorenylmethoxy carbonylating agent

| Starting amino acids | Yield (%) | Melting Point (°C.) | $[\alpha]D^{20}$ (Solvent) | Experimental value C | Theoretical value | |
|---|---|---|---|---|---|---|
| | | | | | H | N |
| L-alanin | 80.0 | 143~144 | -4.0 (ethyl acetate) | 69.45 (69.33 | 5.47 5.41 | 4.50 4.61) |
| L-phenyl alanin | 84.0 | 184~186 | +12.0 (ethyl acetate) | 74.52 (74.33 | 5.43 5.21 | 3.62 3.58) |
| Glycine | 88.0 | 176~177 | — | 68.71 (68.68 | 5.65 5.51 | 4.71 4.80) |
| L-varine | 85.0 | 143~145 | -17.5 (DMF) | 70.82 (70.78 | 6.19 6.03 | 4.13 4.21) |

The invention being thus described, it will be obvious that the same may be varied in many ways. Such variations are not to be regarded as a departure from the spirit and scope of the invention and all such modifications are intended to be included within the scope of the claims.

What is claimed is:

1. A sulfonium compound represented by the general formula:

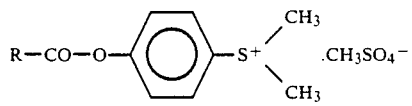

where R represents 9- fluorenylmethoxy group.

* * * * *